United States Patent
Tanaka et al.

(10) Patent No.: US 9,731,077 B2
(45) Date of Patent: Aug. 15, 2017

(54) SYRINGE PLUNGER WITH ONE PIECE HOLLOW GASKET AND PLUNGER ROD

(75) Inventors: Shigeki Tanaka, Osaka (JP);
Masanobu Iwasa, Osaka (JP); Ryohei Namba, Hachi oji (JP); Hidero Kato, Osaka (JP); Teruhisa Hirobe, Osaka (JP)

(73) Assignee: NIPRO CORPORATION, Osaka (JP)

( * ) Notice: Subject to any disclaimer, the term of this patent is extended or adjusted under 35 U.S.C. 154(b) by 1475 days.

(21) Appl. No.: 11/989,689

(22) PCT Filed: Jul. 31, 2006

(86) PCT No.: PCT/JP2006/315172
§ 371 (c)(1),
(2), (4) Date: Sep. 2, 2009

(87) PCT Pub. No.: WO2007/015469
PCT Pub. Date: Feb. 8, 2007

(65) Prior Publication Data
US 2011/0178475 A1    Jul. 21, 2011

(30) Foreign Application Priority Data
Aug. 1, 2005 (JP) ................................. 2005-223087

(51) Int. Cl.
*A61M 5/315* (2006.01)

(52) U.S. Cl.
CPC .... *A61M 5/31511* (2013.01); *A61M 5/31515* (2013.01)

(58) Field of Classification Search
CPC .......... A61M 5/31511; A61M 5/31515; A61M 5/007; A61M 5/145; A61M 5/14546
USPC ................................ 604/222, 223, 228, 233
See application file for complete search history.

(56) References Cited

U.S. PATENT DOCUMENTS

| | | | | |
|---|---|---|---|---|
| 3,348,545 A * | 10/1967 | Sarnoff et al. | ................ | 604/235 |
| 4,636,198 A * | 1/1987 | Stade | ............................ | 604/154 |
| 4,677,980 A * | 7/1987 | Reilly et al. | .................. | 600/432 |
| 5,007,904 A * | 4/1991 | Densmore et al. | ........... | 604/228 |
| 5,094,148 A * | 3/1992 | Haber et al. | ..................... | 92/29 |
| 5,195,975 A * | 3/1993 | Castagna | ....................... | 604/110 |
| 5,201,709 A * | 4/1993 | Capra et al. | ................... | 604/110 |

(Continued)

FOREIGN PATENT DOCUMENTS

| JP | 06-039005 | * 5/1994 |
|---|---|---|
| JP | 2002-272843 | 9/2002 |
| JP | 2005-80957 | 3/2005 |

OTHER PUBLICATIONS

JP 06-039005 May 1994 translation.*

Primary Examiner — Bhisma Mehta
Assistant Examiner — Matthew A Engel
(74) Attorney, Agent, or Firm — Kubovcik & Kubovcik

(57) ABSTRACT

A plunger for a syringe, in which a plunger rod can be prevented by a simple structure from unavoidably falling out of place.

The plunger for a syringe includes the plunger rod and a gasket. The gasket is closed at its upper end and has an inner space, and an opening having a diameter smaller than the diameter of the inner space is provided in the lower end of the gasket. The plunger rod has a collar installed at the tip of the plunger rod. When the collar is positioned in the inner space of the gasket, the plunger rod and the gasket are freely movably fitted together without intimate contact between them.

8 Claims, 8 Drawing Sheets

(56) References Cited

U.S. PATENT DOCUMENTS

| | | | | |
|---|---|---|---|---|
| 5,688,252 | A * | 11/1997 | Matsuda et al. | 604/218 |
| 5,720,731 | A * | 2/1998 | Aramata et al. | 604/191 |
| 5,735,825 | A * | 4/1998 | Stevens et al. | 604/218 |
| 5,738,655 | A * | 4/1998 | Vallelunga et al. | 604/110 |
| 6,432,089 | B1 * | 8/2002 | Kakimi et al. | 604/218 |
| 6,761,707 | B2 * | 7/2004 | Huang et al. | 604/240 |
| 7,141,036 | B2 * | 11/2006 | Berman et al. | 604/60 |
| 7,320,680 | B2 * | 1/2008 | Shue et al. | 604/110 |
| 7,727,202 | B2 * | 6/2010 | Kirchhofer et al. | 604/222 |
| 8,926,569 | B2 * | 1/2015 | Bisegna | A61M 5/31513 604/218 |
| 2003/0233075 | A1 * | 12/2003 | Huegli | 604/222 |
| 2004/0064041 | A1 * | 4/2004 | Lazzaro et al. | 600/432 |
| 2009/0312632 | A1 * | 12/2009 | Hack | 600/432 |
| 2010/0222674 | A1 * | 9/2010 | Cowan et al. | 600/432 |
| 2010/0256486 | A1 * | 10/2010 | Savage | 600/432 |
| 2011/0282317 | A1 * | 11/2011 | Wu | 604/416 |

\* cited by examiner (K−L) > (M−N)

SYRINGE PLUNGER WITH ONE PIECE HOLLOW GASKET AND PLUNGER ROD

This application is a 371 of international application PCT/JP2006/315172 filed Jul. 31, 2006, which claims priority based on Japanese patent application No. 2005-223087 filed Aug. 1, 2005, which is incorporated herein by reference.

TECHNICAL FIELD

The present invention relates to a syringe plunger having a mechanism that prevents coming off of a plunger rod from a gasket and to a prefilled syringe using the same.

BACKGROUND ART

In general, a plunger rod is press-fitted into a gasket in advance and a normal syringe is obtained by inserting the gasket into a barrel. In contrast, a medicinal solution-filled syringe, that is, a prefilled syringe is normally obtained by filling medicinal solution in the barrel, plugging with the gasket, and joining the plunger rod with the gasket. A method of joining the plunger rod with the syringe plugged with the gasket as a post-process is employed as a method of obtaining the prefilled syringe. The reason why this method is employed is that if the plunger rod is attached to the gasket in advance, it is difficult to carry out a gasket plugging process for sealing.

As the method of joining the gasket and the plunger rod of a prefilled syringe as described above, screw-engagement between a female thread of a gasket formed of a rubber elastic material such as butyl rubber or elastomer and a male thread of a plunger rod formed of plastic such as polypropylene is widely employed. It is because, if the plunger rod is press-fitted into the gasket as in the case of a normal syringe, the medicinal solution might be leaked from the gasket or a distal end nozzle by the pressure thereof.

However, the joint between the gasket and the plunger rod by direct screw-engagement in the related art may be loosened due to variation of dimensional tolerance at the time of manufacture or variation in fastening torque of an assembling machine. In such a case, when the prefilled syringe is transported on a motor vehicle for example, the plunger rod is rotated and hence released from screw-engagement due to vibrations or the like applied to the prefilled syringe, so the plunger rod is in danger of coming off. The plunger rod might also come off during manufacture as well.

In order to prevent the plunger rod from coming off, the joint between the gasket and the plunger rod has been studied, and improved joint mechanisms have been proposed. For example, there is proposed a plunger including a plunger rod having a top surface provided with a male thread and a gasket provided with a female thread to be screw-engaged with the male thread, in which the top surface of the plunger rod is provided with a projection projecting toward the distal end thereof and the gasket is provided with a recess to be fitted with the projection, so the gasket and the plunger screw-engaged to each other are hardly disconnected owing to the fitting between the projection and the recess (Patent Document 1).

There is also proposed a syringe including a plunger having a screw-fit portion formed inside a gasket which is to be screw-fitted with a flange formed at the distal end portion of a plunger rod and a space formed on the side of the distal end of the screw-fit portion, in which when the flange formed on the distal end portion of the plunger rod is advanced to the space beyond the screw-fit portion, the flange is engaged with the space in a loosely fitted state, so an external force exerted on the plunger rod is prevented from being transmitted directly to the gasket (Patent Document 2).

Patent Document 1: JP-A-2005-80957
Patent Document 2: JP-A-2002-272843

DISCLOSURE OF INVENTION

Problem to be Solved by the Invention

However, with the structure of the plunger adapted to prevent the gasket and the plunger rod screw-fitted to each other from easily being disconnected by the engagement between the projection and the recess as in Patent Document 1, when a force in the direction of rotation is applied to the plunger rod, it also provides a rotating force directly to the gasket. Therefore, when the rotating force in the direction opposite from the screw-in direction is applied to the plunger rod, the screw-engagement between the plunger rod and the gasket is inevitably released. In addition, when the syringe is set on a syringe pump for example, the screw-engagement between the plunger rod and the gasket may be loosened by rotating the plunger. Because a plunger rod fitting section of the syringe pump is configured to fit a vertical rib of the plunger rod and the syringe cannot be set in the syringe pump without rotating the plunger. As a result of the looseness, fluctuation of amount of discharge from the syringe may occur.

As in Patent Document 2 with the structure in which the flange formed on the distal end portion of the plunger rod is advanced into the space in the gasket beyond the screw-fit portion, when the plunger rod and the gasket plugged into the barrel are screw-fitted, it is necessary to incline the plunger rod with respect to the barrel in the barrel for achieving screw-fitting. Therefore, when a plunger rod having substantially the same size as the inner radius of the barrel is employed, the plunger rod cannot be inclined in the barrel, and hence it is difficult to screw-fit the flange formed on the distal end portion of the plunger rod with the screw-fit portion and to allow the flange to advance into the space beyond the screw-fit portion. Therefore, a structure which prevents the plunger rod from coming off and allows the plunger rod and the gasket to be joined without inclining the plunger rod is required. Furthermore, it is desired to be able to provide a rotating force to the gasket as needed.

It is an object of the invention to provide a syringe plunger which is capable of preventing a plunger rod from coming off due to an accidental force in a simple structure and to provide a syringe and a prefilled syringe having the plunger.

Means for Solving the Problem

Accordingly, the inventors devised as follows. By using a syringe plunger including a plunger rod and a gasket, in which the gasket includes an internal spacer with a closed upper end and an opening having a diameter smaller than the diameter of the inner space at a lower end thereof, the plunger rod includes a collar attached at a distal end thereof, the collar is inserted in the inner space of the gasket, and the plunger rod having the collar at the distal end thereof and the gasket are in a loosely fitted state, because whether smooth movement of the collar in the inner space of the gasket is impaired or achieved is determined depending on the state of press contact between the collar and the gasket when a rotating force is applied to the plunger rod, the plunger rod is easily attached to the gasket when manufacturing, and is prevented from coming off when being mounted to a syringe pump and transported. And with the collar existing in the inner space of the gasket and being attached to the plunger rod, the plunger rod having the collar at the distal end thereof and the gasket are brought into a loosely fitted state, so a joint between the plunger to rod and the gasket is easily achieved.

Since the syringe and a prefilled syringe using the above-described plunger rod are free from coming off of the plunger rod, they can be used in syringe pumps or injections with easier operation.

Advantages of the Invention

Because the plunger of the invention has the structure in which the collar is provided between the gasket and the plunger rod, and the collar slips, there is no possibility of coming off of the plunger rod, and hence it is suitably used. The syringe plunger of the invention and the syringe and the prefilled syringe using the same are suitable for medical use, because the collar is provided in the gasket and the plunger rod and the gasket are not directly connected as descried above so that the slip and the rotation of the collar is manipulated.

Figure 1:
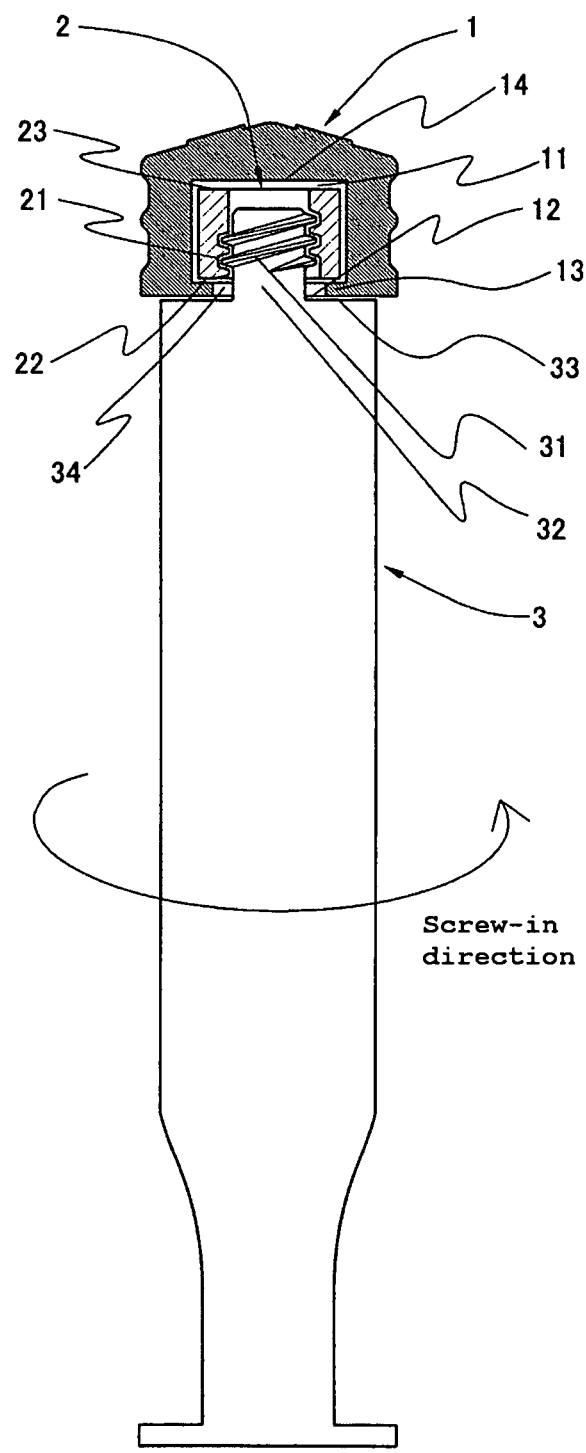
FIG. 1 It is a vertical cross-sectional view of an embodiment of a syringe plunger in the invention.

REFERENCE NUMERALS 1 gasket
2 collar
2' collar
3 plunger rod
4 prefilled syringe
5 top cap
11 inner space
12 opening
13 annular rib
14 ceiling surface
21 female thread
22 collar bottom face
23 collar top face
31 male thread
32 male thread base portion
33 top face of plunger rod
34 gap
41 barrel
42 injection port
43 flange
44 retaining portion

BEST MODE FOR CARRYING OUT THE INVENTION

Referring now to the drawings, a syringe plunger and a prefilled syringe using the same according to the invention will be described. However, the invention of the present application is not limited to embodiments shown in the drawings.

Figure 2:
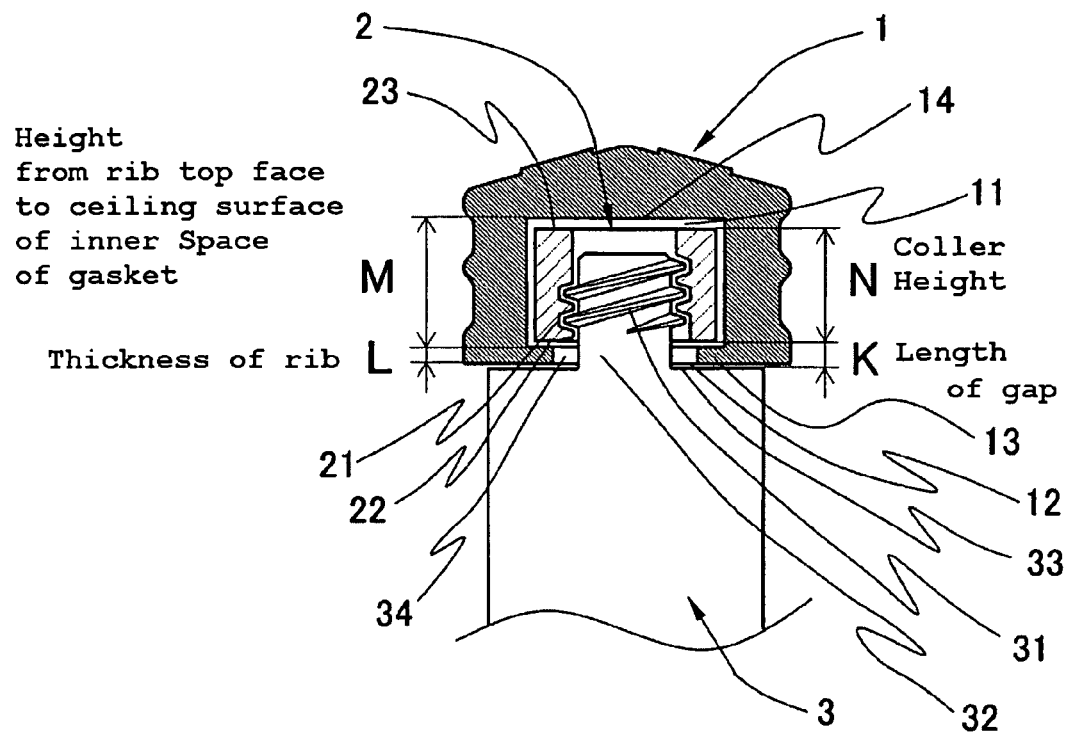
FIG. 2 It is an enlarged view of the distal end of the syringe plunger shown in FIG. 1.
Figure 3A:
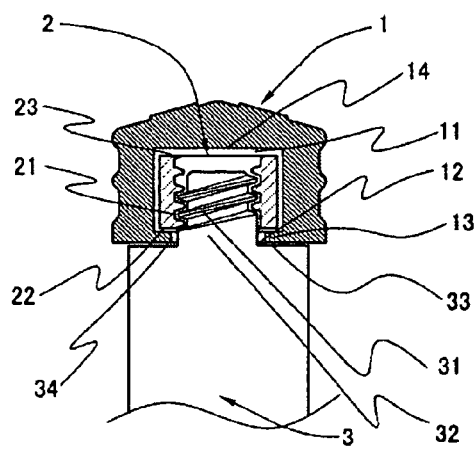
FIG. 3 (a)-(c) They are partially enlarged vertical cross-sectional views showing the syringe plunger of the invention according to other embodiments.
Figure 3B:
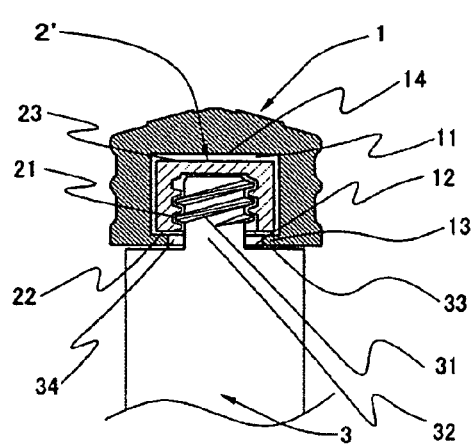
Figure 3C:
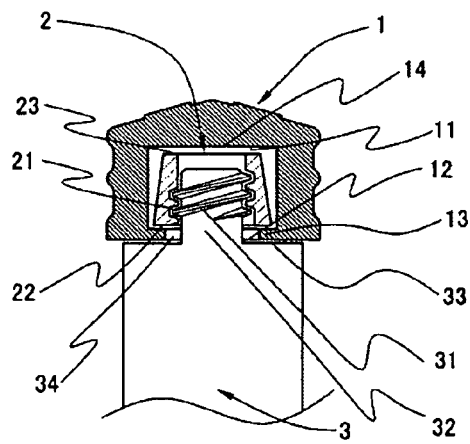
Figure 6A:
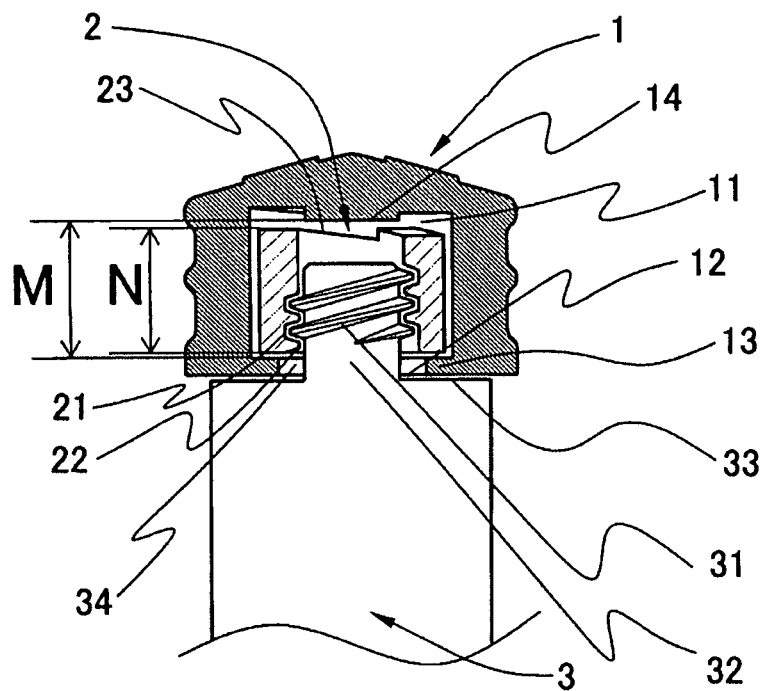
FIG. 6 (a) It is a partially enlarged vertical cross-sectional view according to still another embodiment of the syringe plunger in the invention. (b) It is a perspective view of a collar used in the embodiment shown in FIG. 6(a).
Figure 6B:
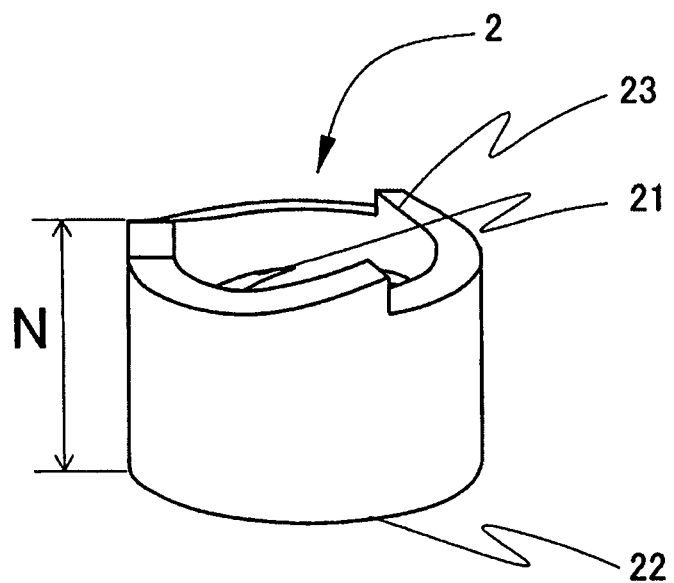
Figure 7A:
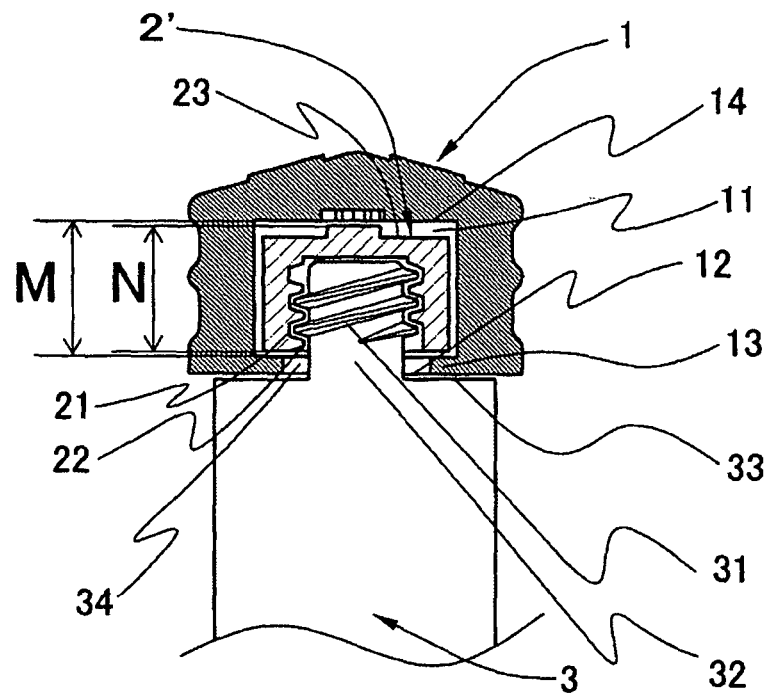
FIG. 7 (a) is a partially enlarged vertical cross-sectional view according to still another embodiment of the syringe plunger in the invention. (b) It is a perspective view of a collar used in the embodiment shown in FIG. 7(a).
Figure 7B:
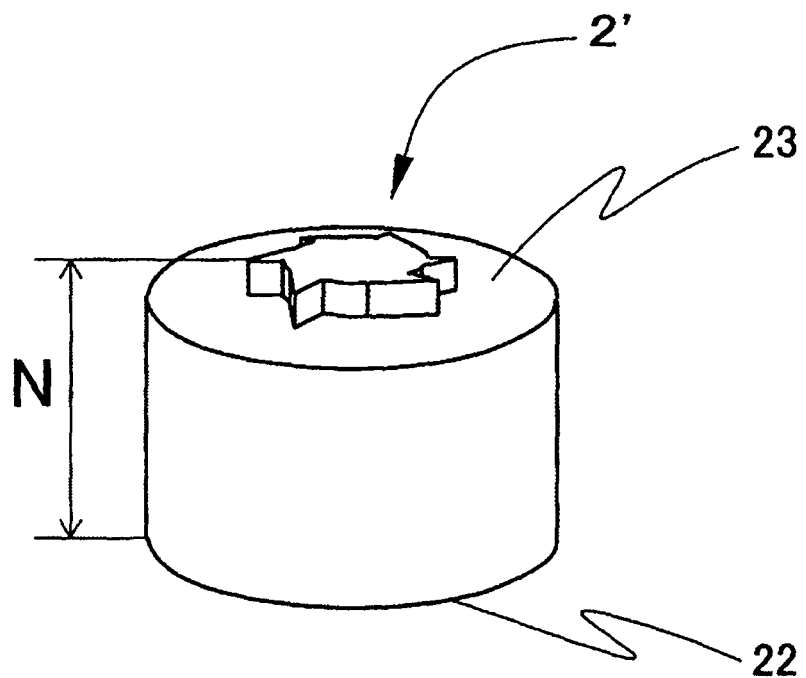
Figure 8:
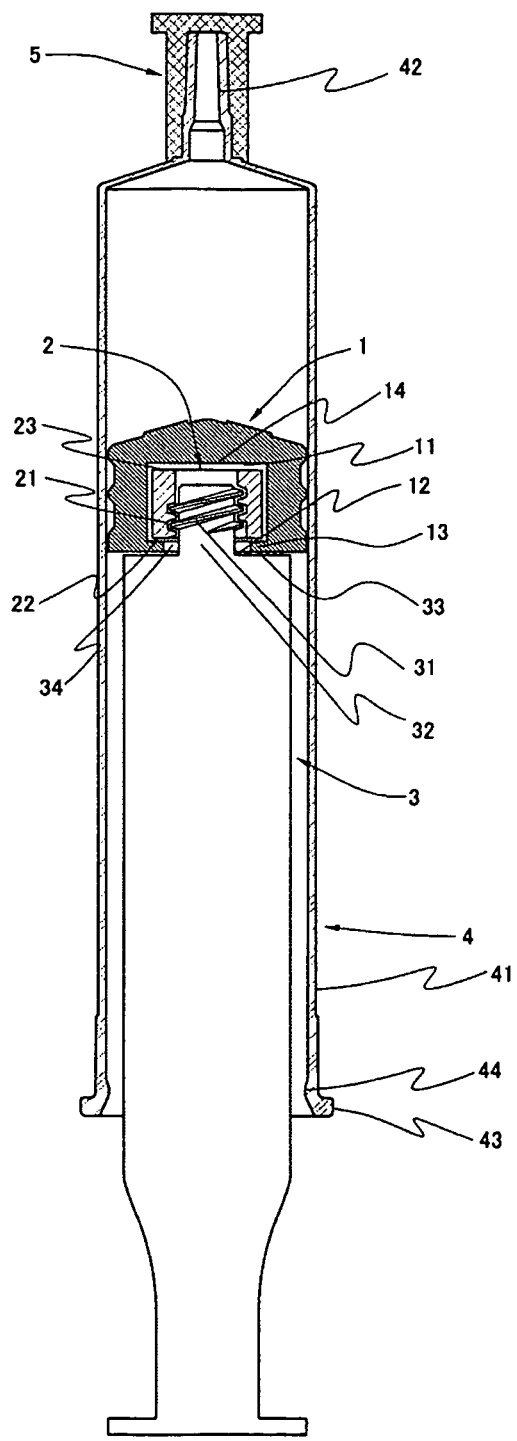
FIG. 8 It is a vertical cross-sectional view showing an embodiment of a prefilled syringe using the syringe plunger shown in FIG. 1

FIG. 1 is a vertical cross-sectional view of an embodiment of the syringe plunger in the invention. FIG. 2 is an enlarged view of the distal end of the plunger. FIGS. 3(a) to (c) are partially enlarged vertical cross-sectional views illustrating screw-engaged states between a plunger rod and a collar according to other embodiments. FIG. 4 to FIG. 7 each show a vertical cross-sectional view of a projection on a collar top face and a recess on a ceiling surface of a gasket and a perspective view of the collar according to another embodiment. FIG. 8 is a vertical cross-sectional view showing an embodiment of the syringe plunger according to the invention.

FIG. 1 illustrates the syringe plunger composed of a combination of a gasket 1, a collar 2, and a plunger rod 3. The gasket 1 includes an inner space 11 closed on top thereof, and the gasket 1 is formed with an opening 12 being smaller in diameter than the inner space 11 at the lower end of the gasket 1. The gasket shown in FIG. 1 is formed into a cylindrical hollow member and includes an annular rib 13 at the opening 12. The inner space 11 communicates with the outside via the opening 12. The hollow collar 2 having an opening at least at the lower end thereof is stored in the inner space 11 formed above the annular rib 13, and is prevented from coming off by the annular rib 13. A female thread 21 is formed inside the collar. The collar 2 is attached by screw-engaging to the plunger rod 3 having a male thread 31 to be screw-engaged with the female thread 21 at the distal end thereof, and the plunger rod 3 having the collar 2 attached to the distal end thereof is loosely fitted to the gasket 1. In FIG. 1, a gap 34 is defined by a bottom face 22 of the collar attached to the plunger rod, a plunger rod top face 33, and a male thread base portion 32 at a proximal end of the male thread. The annular rib 13 of the gasket 1 is fitted into the gap 34, and the annular rib 13, the bottom face 22 of the collar, the male thread base portion 32 and the top face of plunger rod 33 exist in the interior of the gap 34 without coming into tight contact with each other. With the structure in which the plunger rod 3 having the collar 2 attached to the distal end thereof is loosely fitted to the gasket, even when an external force is applied to the plunger rod, the collar attached to the distal end of the plunger rod slips in the gasket, so the collar and the plunger rod are not disconnected from each other. Therefore, the plunger rod is prevented from coming off during transportation, and the possibility of disconnection of the joint between the plunger rod 3 and the collar 2 is avoided when setting a syringe in a syringe pump (not shown).

The gasket 1 is a rubber elastic member, and may be formed of a resin having rubber elasticity which is used for normal syringe gaskets as a material. The rubber elastic member has liquid-tight properties, and hence materials such as butyl rubber, butadiene rubber, isoprene rubber, silicone rubber, thermoplastic elastomer, and silicone elastomer are applicable. The material of plunger rod 3 is not limited specifically as long as it can be used for the syringe, and hence. However, thermoplastic resin is preferable because of easiness of molding.

The syringe plunger of the invention may be obtained by inserting the collar 2 into the inner space 11 of the gasket 1 and then screw-engaging the male thread 31 at the distal end of the plunger rod 3 with the female thread 21 of the collar 2, and may be obtained by screw-engaging the male thread 31 at the distal end of the plunger rod 3 with the female thread 21 of the collar 2 and then inserting the collar 2 screw-engaged to the distal end of the plunger rod 3 into the inner space 11 of the gasket 1. The method of attaching the collar to the plunger rod is not limited to screw-engagement. There are a method of forming a hole (depression) and a claw which engages the hole (depression) on the collar and the plunger rod, respectively, and engaging the collar and the plunger rod, and a method of forming the collar into a shape which is fitted to the plunger rod, and bonding to the inner wall of the collar. However, the method of screw-engaging the collar and the plunger rod is specifically preferable since the plunger rod is detachable from the collar as needed.

The syringe plunger of the invention is obtained normally by inserting the collar 2 into the inner space 11 of the gasket 1 and then screw-engaging the male thread 31 at the distal end of the plunger rod 3 with the female thread 21 of the collar 2. When screw-engaging the male thread 31 with the female thread 21, the collar 2 is pushed by the plunger rod 3 against a ceiling surface 14 of the inner space 11 of the gasket 1. When a collar top face 23 is pressed against the ceiling surface 14 of the inner space 11 of the gasket 1, the smooth movement of the collar 2 with respect to the ceiling surface 14 of the gasket is impaired by friction, and hence the plunger rod 3 and the collar 2 are engaged easily without slipping of the collar 2 in the inner space 11 of the gasket 1. In the state of screw-engagement, the release of the screw-engagement is easily by rotating the plunger rod 3 in the direction opposite from the screw-in direction while pressing the same.

The relation of lengths is $(K-L)>(M-N)$, where K is the length of the gap, L is the thickness of the rib, M is the height from the rib top face to the ceiling surface of the inner space of the gasket, and N is the height of the collar, so as to avoid tight contact between the plunger rod top face 33 and the opening 12 of the gasket for enabling the screw-engagement and release of the screw-engagement between the gasket 1 and the collar 2 when screw-engaging the gasket 1 and the collar 2 or when they are in the screw-engaged state. It is preferable that the distal end of the male thread 31 does not protrude beyond the collar top face 23 in a state of screw-engagement between the collar 2 and the plunger rod 3 so that only the collar 2 comes into contact with the ceiling surface 14 of the inner space 11 of the gasket 1. Therefore, a configuration in which a groove of the female thread of the collar 2 does not exist on the upper portion of the collar is applicable so that the male thread 31 of the plunger rod 3 does not screw into the upper portion of the collar 2 (FIG. 2).

FIGS. 3(*a*) and (*b*) are partially enlarged vertical cross-sectional views showing a state in which the collar 2 and the plunger rod 3 of the syringe plunger of the invention are screw-engaged, which is another embodiment of the structure in which the distal end of the male thread does not protrude beyond the collar top face in the state of screw-engagement between the collar and the plunger rod. Screwing the male screw into the upper portion of the collar may be restricted by a structure in which the thickness of the side wall of the upper portion of the collar is increased (not shown), or a structure in which the diameter of the male thread base portion 32 is increased as shown in FIG. 3(*a*) in addition to the structure in which the groove does not exist in the upper portion of the collar as shown in FIG. 2. As shown in FIG. 3(*b*), in the case of using a collar 2' having a closed upper end, the plunger rod 3 and the gasket 1 do not come into direct contact with each other when they are screw-engaged even when the male thread portion of the plunger rod 3 is longer than the female thread portion of the collar 2, so the loosely fitted state described above is easily achieved.

The contour of the collar 2 is not specifically limited, but a circular cylinder shape or polygonal, at least hexagonal column shape, is preferable. However, the gasket may be damaged when the collar has angular portions, and hence the circular cylinder shape is specifically preferable. The outside surface of the collar may be formed into a tapered shape having the diameter decreased toward the distal end so as to allow easy insertion of the gasket into the space, as shown in FIG. 3(*c*).

Smooth movement of the collar in the space of the gasket is impaired when the collar is in press-contact with the gasket, and the collar slips in the space of the gasket when they are not in press-contact with each other. Therefore, when the plunger rod is rotated while pressing, the gasket is brought into press-contact with the collar and hence the screw-engaging and release of the screw-engaging between the collar and the plunger rod are enabled. In contrast, when the plunger rod is not pressed, the gasket is not brought into press-contact with the collar and hence the screw-engagement therebetween is not released unintentionally.

Figure 4A:
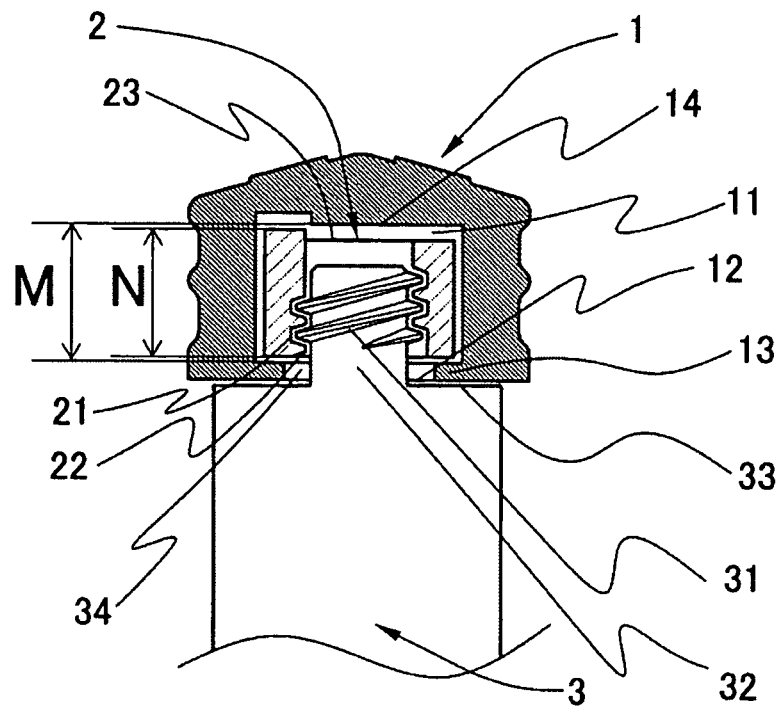
FIG. 4 (a) It is a partially enlarged vertical cross-sectional view according to another embodiment of the syringe plunger in the invention. (b) It is a perspective view of a collar used in the embodiment shown in FIG. 4(a).
Figure 4B:
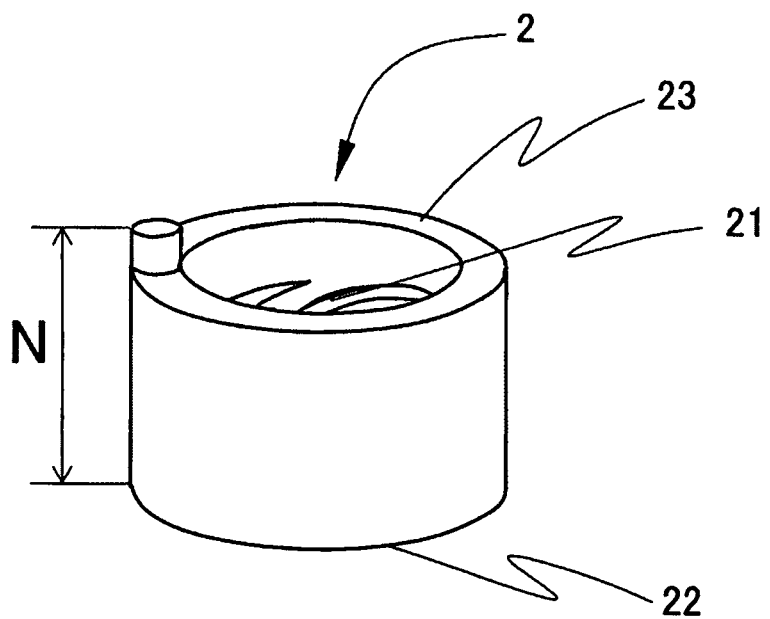
Figure 5A:
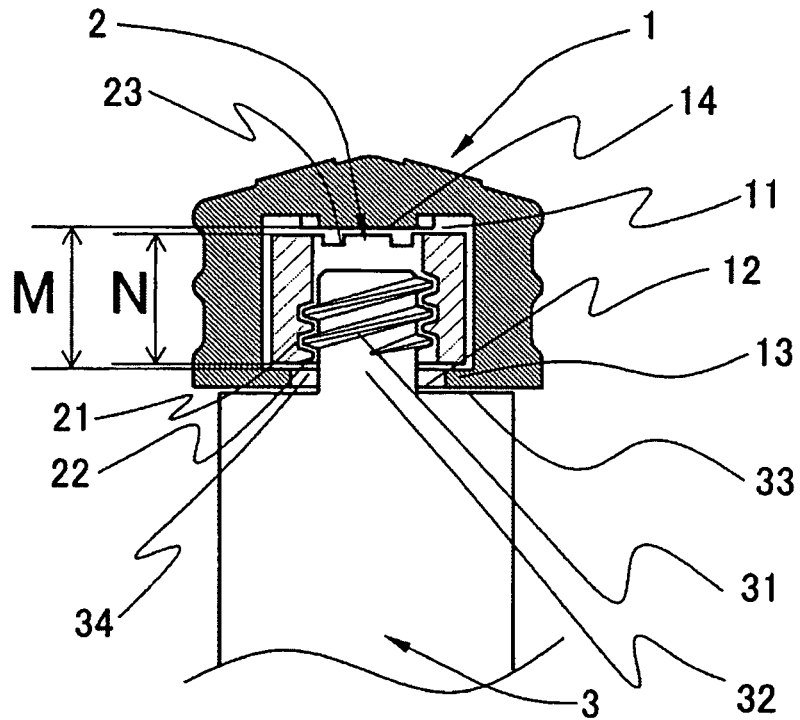
FIG. 5 (a) It is a partially enlarged vertical cross-sectional view according to still another embodiment of the syringe plunger in the invention. (b) It is a perspective view of a collar used in the embodiment shown in FIG. 5(a).
Figure 5B:
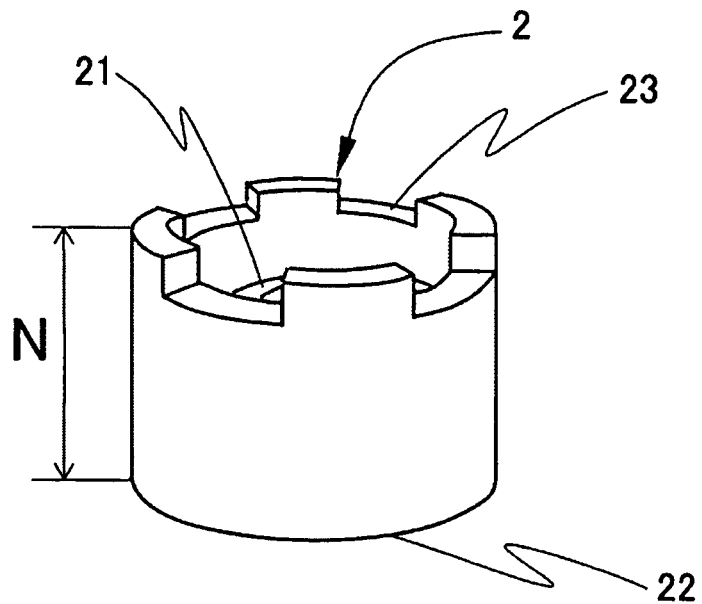

The smooth movement can be impaired by a frictional force between the gasket 1 and the collar 2. However, in order to ensure impairment, a configuration in which the collar top face is formed with a projection and the ceiling surface of the gasket is formed with a recess which engages or fits to the projection is applicable. When forming the projection and the recess, the height M from the rib top face to the ceiling surface of the inner space of the gasket corresponds to the height from the rib top face to the ceiling surface except for the recess formed on the ceiling surface, and the height N of the collar corresponds to the height to the top of the projection formed on the collar top face. FIG. 4 to FIG. 7 show embodiments of the projection on the collar top face and the recess on the ceiling surface of the gasket. It is possible to form a single projection at the end of the collar top face as shown in FIG. 4, and a plurality of projections may be formed at the end of the top face as shown in FIG. 5. Alternatively, projections each having the shape of right-angled triangle column laid down so that the vertical surface is oriented in the screw-in direction may be formed as shown in FIG. 6. A projection of a gear shape which has teeth projecting toward the circumference may be formed at the center of the collar top face having the closed upper end as shown in FIG. 7. In the case of the collar having the closed upper end as shown in FIG. 7, at least one projection may be formed on the top face at random. In the case of forming a plurality of projections, the shapes and intervals of the respective projections may not be the same. However, when considering easiness of engagement or fitting, regular shapes and intervals are preferable. The recess may be of any shape as long as it is engaged with or fitted to the projection. However, the same shape as the projection is preferable. The number of the recesses may be larger than the projections as long as engagement or fitting is enabled.

When a number of small projections which are the same shape as each other are formed regularly on the collar, the projections and the recess are engaged or fitted easily. Therefore, the time required for medical procedure is reduced and, simultaneously, the burden of engagement or fitting may be removed. When a small number of projections are formed, the influence of variation in dimensions of the projections on fitting (engagement) is not much. Therefore, accuracy is not required for manufacture, and there is no possibility of disappearance of the projections and the recesses due to abrasion. Therefore, although the number of the projections is not specified, three or more projections are preferable in order to avoid easy disconnection of fitting between the projections of the collar and the recess of the gasket and to apply a pressing force and a rotating force uniformly to the gasket when a rotating force is applied to the plunger rod while pressing the plunger rod. More preferably, the projections are formed into the same shape at regular intervals. The shape of the projections preferably includes a substantially vertical surface in the screw-in direction in order to enhance impairment of slip of the collar, and is preferably a triangular prism which is laid down or a column shape.

When forming the projection on the top face of a collar having a closed upper end, a plurality of projections may be formed on the top face at regular intervals or a gear shaped projection may be formed at the center of the top face as shown in FIG. 7 in addition to forming the projection at the end of the top face as in the case of a collar having an opened upper end. When the projection of the gear shape is formed on the top face, with the projection formed at the center, the collar can be brought into stable press contact with the ceiling surface of the inner space of the gasket when the plunger rod is pressed. Since the teeth formed in the direction of circumference of the projection exert a force on the gasket in the direction of rotation, when a rotating force is applied to the plunger rod, the number of teeth of the gear affects further the firm impairment of the smooth movement between the collar and the gasket and the rotating force of the gasket. When a number of small teeth are formed, the projections and the recesses are engaged or fitted easily so the time required for medical procedure is reduced, and the burden of engagement or fitting may be removed. When a small number of projections are formed, the influence of variation in dimensions of the projections on fitting (engagement) is not much. Therefore, accuracy is not required for manufacture, and there is no possibility of disappearance of the teeth of the projection and the recesses which fit (engage) the teeth due to abrasion. Consequently, although the number of teeth is not specified and the shapes and intervals may be irregular, three or more teeth are preferable in order to avoid easy disconnection of fitting (engagement) between the projections of the collar and the recess of the gasket and to apply a rotating force uniformly to the gasket when a rotating force is applied to the plunger rod while pressing the plunger rod. More preferably, the teeth are preferably formed into the same shape at regular intervals. The shape of the teeth preferably has a substantially vertical surface in the screw-in direction in order to enhance impairment of the smooth movement of the collar. Alternatively, a configuration in which a projection of the gear shape is formed at the center of the collar top face and projections each having a substantially vertical surface in the screw-in direction are formed at the end of the top face is also applicable.

In order to impair firmly the smooth movement of the collar 2 in the inner space of the gasket 1, it is also possible to provide a recess on the collar top face and a projection to be fitted to the recess on the ceiling surface of the gasket in the same manner as providing the projection on the collar top face and the recess to be fitted to the projection on the ceiling surface of the gasket. In other words, the fitting portion (the recess and the projection) between the collar and the gasket described above may be reversely formed. When forming the projection and the recess, the height M from the rib top face to the ceiling surface of the inner space of the gasket corresponds to the height from the rib top face to the top of the projection formed on the ceiling surface, and the height N of the collar corresponds to the height except for the recess formed on the collar top face. Alternatively, a rubber material or the like having a large frictional force may be adhered on the collar top face or the ceiling surface of the gasket instead of forming the projection and the recess on the collar top face and the ceiling surface of the gasket.

The invention also provides a prefilled syringe using the above described syringe plunger, and an embodiment is shown in FIG. 8. A barrel 41 used in a prefilled syringe 4 is of a cylindrical shape provided with an injection port 42 having a small diameter at the distal end thereof and opening at the proximal end, and includes a flange 43 for placing fingers thereon at the proximal ends and an annular gasket retaining portion 44 inside the portion near the proximal opening formed integrally therewith. The injection port is attached with a detachable cap 5. The gasket 1 is slidably stored in the interior of the barrel 41, the outer periphery of the gasket is in tight contact with the interior of the barrel, and medicinal solution is contained in a space surrounded by the gasket and the barrel. The gasket 1 is a cylindrical hollow member closed at the upper end thereof and opened at the lower end thereof, which includes the annular rib 13 at the opening thereof. The collar 2 of a hollow member shape having an opening at least at the lower end thereof is stored in the space 12 formed above the annular rib 13 and the female thread 21 is provided inside the collar which is a hollow member shape. The collar 2 is attached by screw-engaging to the plunger rod 3 having the male thread 31 to be screw-engaged with the female thread 21 at the distal end thereof, and the plunger rod 3 provided with the collar at the distal end thereof is in a loosely fitted state with the gasket 1. The gap 34 is defined by the bottom face 22 of the collar 2 and the plunger rod top face 33 screw-engaged to each other and the male thread base portion 32 as the proximal end of the male thread, and the annular rib 13 of the gasket is inserted into the gap, and the annular rib 13, the bottom face 22 of the collar, the male thread base portion 32 and the plunger rod top face 33 exist in the gap 34 without coming into tight contact with each other.

Manufacture of the above described prefilled syringe is performed by filling medicinal solution in the barrel 4, and plugging the gasket 1 in which the collar 2 is inserted in the space 12 in advance into the barrel 4 in the state of being slidable. Then, the male thread 31 of the plunger rod 3 is screw-engaged to the female thread 21 of the collar 2, so the prefilled syringe is obtained.

When screwing the male thread 31 into the female thread 21, the collar is pressed toward the ceiling surface of the space of the gasket by the plunger rod. When the collar top face is brought into press-contact with the ceiling surface of the space in the gasket, smooth movement of the collar with respect to the ceiling surface 14 of the gasket is impaired by friction. Therefore, the screw-engagement of the plunger rod and the collar is easily achieved without causing slipping of the collar in the space inside the gasket. When the plunger rod is rotated in the direction opposite from the screw-in direction while pressing the plunger rod in the screw-engaged state, the screw-engagement is easily released.

In the case of a collar formed with a projection having a substantially vertical surface in the screw-in direction, the screw-engagement is easily achieved. When the gasket is strongly adhered to the inner surface of the barrel, a rotating force is provided to the gasket by rotating the plunger rod in the screw-in direction while pressing the plunger rod, and hence separation of the gasket from the barrel is achieved by rotating the gasket in the barrel. Therefore, it is not necessary to separate the gasket by pushing or pulling the plunger rod, and hence medicinal solution is free from contamination. In particular, in the case of the collar formed with the projection having substantially vertical surfaces both in the screw-in direction and the direction opposite from the screw-in direction as shown in FIG. 4 and FIG. 5, not only the separation of the gasket, but also the screw-engagement and the release of the screw-engagement between the plunger rod and the collar are easily achieved.

The plunger shown above may be used for normal syringes—not only for a prefilled syringe. Even when it is used for a syringe other than a prefilled syringe, the plunger rod is prevented from coming off, and loosening of the screw-engagement due to the rotation of the plunger hardly occurs during usage of the syringe. In addition, when the collar is attached to the plunger rod via screw-engagement, the screw-engagement is easily released by rotating the plunger rod in the direction opposite from the screw-in direction while pressing the plunger rod after the usage of the syringe. Therefore, it is possible to remove only the plunger rod for disposition, and hence the disposal after usage of the syringe is easy.

With the structure of the plunger as described above, when attaching the plunger rod to the gasket plugged in the barrel, the plunger rod can be attached to the gasket without inclining the plunger rod and, in addition, the gasket and the plunger rod are joined in a loosely fitted state, and it is not necessary to reduce the thickness of the plunger rod. Therefore, disadvantages such that the plunger rod is wobbled in the barrel and hence stability is lost because of a reduction of the thickness thereof, thereby lack of stability while being stored or used, and the gasket is distorted due to an unstable plunger rod are avoided.

When setting the above-described syringe or the prefilled syringe to the syringe pump, the plunger rod fitting section of the syringe pump is configured to fit the vertical rib of the plunger rod. Therefore, the syringe cannot be set in the syringe pump without rotating the plunger. In this case, the screw-engagement between the plunger rod and the gasket may be loosed by rotating the plunger. However, with the structure described above, the collar slips and hence the setting is achieved without affecting the plunger.

The syringe plunger, the syringe and the prefilled syringe using the same of the invention are preferably used in the medical field by providing the collar in the gasket, not joining the plunger rod and the gasket directly joined to each other, and manipulating slipping and rotation of the collar are desired as described above.

The invention claimed is:

1. A syringe plunger consisting essentially of a plunger rod and a gasket;
    wherein the gasket is a one-piece cylindrical hollow member formed of a resin having rubber elasticity, said gasket having a closed upper end formed by an inner ceiling surface; a lowermost end; and having a cylindrical inner space; said gasket at the lowermost end thereof being provided with an opening having a diameter smaller than a diameter of the cylindrical inner space, said opening being formed by an inwardly extending annular rib formed on an inner surface of the gasket at the lowermost end thereof, the annular rib having a top face and a bottom face and a thickness L; and wherein
    the plunger rod comprises a cylindrical collar attached to a distal end of the plunger rod, the collar being positioned entirely within the cylindrical inner space and having a collar top face, a collar bottom face and an annular side wall between the collar top face and collar bottom face, an outer diameter of the annular side wall being greater than the diameter of said opening and smaller than the diameter of the cylindrical inner space, the collar having a height N from the collar bottom face to the collar top face, with a top face of the plunger rod and the collar bottom face forming a gap K; wherein
    the outer diameter of the annular side wall of the collar is less than the inner diameter of the cylindrical inner space and greater than the diameter of the opening and, when the height of the cylindrical inner space from the top face of the annular rib to the inner ceiling surface of the gasket is M, the syringe plunger satisfies the following relationship: (K−L)>(M−N).

2. The syringe plunger according to claim 1, wherein smooth movement of the collar with respect to the inner ceiling surface of the gasket is impaired and slipping of the collar is controllable when the collar top face is brought into press contact with the inner ceiling surface of the cylindrical inner space of the gasket.

3. The syringe plunger according to claim 1, wherein a projection is provided on the collar top face and a recess to be engaged or fitted to the projection is provided on the inner ceiling surface of the gasket.

4. The syringe plunger according to claim 1, wherein a recess is provided on the collar top face and a projection to be engaged or fitted to the recess is provided on the inner ceiling surface of the gasket.

5. The syringe plunger according to claim 1, wherein the annular side wall of the collar is formed into a tapered shape reducing in diameter thereof toward a distal end thereof.

6. The syringe plunger according to claim 1, wherein the plunger rod and the collar are attached by a screw-engagement between a male thread provided at the distal end of the plunger rod and a female thread provided inside the collar.

7. The syringe plunger according to claim 6, wherein the screw-engagement and release of the screw-engagement between the plunger rod and the collar are freely achieved when the collar top face is brought into press contact with the inner ceiling surface of the inner space of the gasket.

8. A syringe including the syringe plunger according to claim 1, the syringe having a barrel and the syringe plunger being inserted into the barrel so as to be liquid-tight and slidable with the gasket being in direct contact with the barrel.

* * * * *